United States Patent
VanTassel et al.

(10) Patent No.: US 6,949,087 B2
(45) Date of Patent: Sep. 27, 2005

(54) APPARATUS WITH WEEPING TIP AND METHOD OF USE

(75) Inventors: Robert A. VanTassel, Excelsior, MN (US); David R. Holmes, Jr., Rochester, MN (US); Robert S. Schwartz, Rochester, MN (US)

(73) Assignee: Tricardia, LLC, Excelsior, MN (US)

( * ) Notice: Subject to any disclaimer, the term of this patent is extended or adjusted under 35 U.S.C. 154(b) by 0 days.

(21) Appl. No.: 10/855,026

(22) Filed: May 26, 2004

(65) Prior Publication Data

US 2004/0220536 A1 Nov. 4, 2004

Related U.S. Application Data

(60) Continuation of application No. 10/342,023, filed on Jan. 14, 2003, now Pat. No. 6,855,132, which is a continuation of application No. 09/829,022, filed on Apr. 9, 2001, now Pat. No. 6,547,769, which is a division of application No. 09/468,688, filed on Dec. 20, 1999, now Pat. No. 6,241,710.

(51) Int. Cl.$^7$ ................................................ A61M 5/32
(52) U.S. Cl. ....................................................... 604/272
(58) Field of Search ........................ 604/29, 30, 53–55, 604/93, 118, 121, 264, 272, 271, 273; D24/112

(56) References Cited

U.S. PATENT DOCUMENTS

| | | |
|---|---|---|
| 1,124,851 A | 1/1915 | Burkle |
| 1,192,596 A | 7/1916 | Albrecht |
| 1,370,788 A | 3/1921 | Good et al. |
| 2,112,629 A | 3/1938 | Lloyd |
| 3,076,457 A | 2/1963 | Copen |

(Continued)

FOREIGN PATENT DOCUMENTS

| | | |
|---|---|---|
| EP | 271775 A2 | 6/1988 |
| EP | 699449 A1 | 3/1996 |

(Continued)

OTHER PUBLICATIONS

Hansen et al., New High–Flow "Cloud" Catheter for Safer Delivery of Contrast Material, Cardiovascular Radiology, Nov. 1989, pp. 461–464, vol. 173, No. 2.

(Continued)

*Primary Examiner*—Sharon Kennedy
(74) *Attorney, Agent, or Firm*—Inskeep IP Group, Inc.

(57) ABSTRACT

The invention provides surgical needles with a porous distal portion from which a liquid injectate will weep or ooze multidirectionally under injection pressure while the porous distal portion of the needle is inserted into a body surface. The porous distal portion of the needle can be fabricated from a porous carbon, metal, ceramic or polymer and preferably has a decreasing gradient of impedance to fluid flowing to the point of the needle to compensate for the falling off of injection pressure as fluid moves towards the point, thereby ensuring uniform weeping of the injectate along the injection course. The needle is adapted for attachment to a catheter or syringe. In another embodiment, a surgical assemblage is provided wherein a porous distal portion having similar fluid flow characteristics is located along the distal end of a catheter, and a needle point is attached to the distal end of the catheter (e.g., a steerable catheter) for piercing tissue. A guidance catheter can be used to direct the invention devices to a remote internal injection site. The invention devices and methods can be used to inject fluids (including those containing nucleic acids for gene therapy) into interior body walls or tissue, such as a beating heart, without substantial loss of fluid and without substantial damage to tissue caused by injectate.

41 Claims, 1 Drawing Sheet

U.S. PATENT DOCUMENTS

| | | |
|---|---|---|
| 4,186,745 A | 2/1980 | Lewis et al. |
| 4,256,102 A | 3/1981 | Monaco |
| 4,411,657 A | 10/1983 | Galindo |
| 4,512,768 A | 4/1985 | Rangaswamy |
| 4,717,379 A * | 1/1988 | Ekholmer .................... 604/43 |
| 4,838,877 A | 6/1989 | Massau |
| 5,069,673 A | 12/1991 | Shwab |
| 5,085,635 A | 2/1992 | Cragg |
| 5,156,597 A | 10/1992 | Verreet et al. |
| 5,254,106 A | 10/1993 | Feaster |
| 5,380,307 A | 1/1995 | Chee et al. |
| 5,389,074 A | 2/1995 | Parker et al. |
| 5,569,197 A | 10/1996 | Helmus et al. |
| 5,603,703 A | 2/1997 | Elsberry et al. |
| 5,643,228 A | 7/1997 | Schucart et al. |
| 5,662,619 A | 9/1997 | Zarate |
| 5,713,861 A | 2/1998 | Vanarthos |
| 5,735,831 A | 4/1998 | Johnson et al. |
| 5,738,649 A | 4/1998 | Macoviak |
| 5,800,407 A | 9/1998 | Eldor |
| 5,817,074 A | 10/1998 | Racz |
| 5,885,252 A | 3/1999 | Liu |
| 5,957,901 A | 9/1999 | Mottola et al. |
| 5,989,209 A | 11/1999 | Barrett |
| 6,010,495 A | 1/2000 | Tilton, Jr. |
| 6,162,202 A | 12/2000 | Sicurelli et al. |
| 6,179,816 B1 | 1/2001 | Mottola et al. |
| 6,210,376 B1 | 4/2001 | Grayson |
| 6,224,608 B1 | 5/2001 | Ciccolella et al. |
| 6,241,710 B1 | 6/2001 | Van Tassel et al. |

FOREIGN PATENT DOCUMENTS

| | | |
|---|---|---|
| EP | 727187 A1 | 8/1996 |
| WO | WO 90/11092 | 10/1990 |
| WO | WO 96/31247 | 10/1996 |
| WO | WO 97/18004 | 5/1997 |
| WO | WO 99/19016 | 4/1999 |

OTHER PUBLICATIONS

Wolff et al., "Direct Gene Transfer into mouse Muscle in Vivo," Science 247:1465–1468 (1990).

Seeger et al., "The Cloned Genome of Ground Squirrel Hepatitis Virus is Infectious in the Animal" Proc. Natl. Acad. Sci. USA 81:5849–5852 (1984).

* cited by examiner

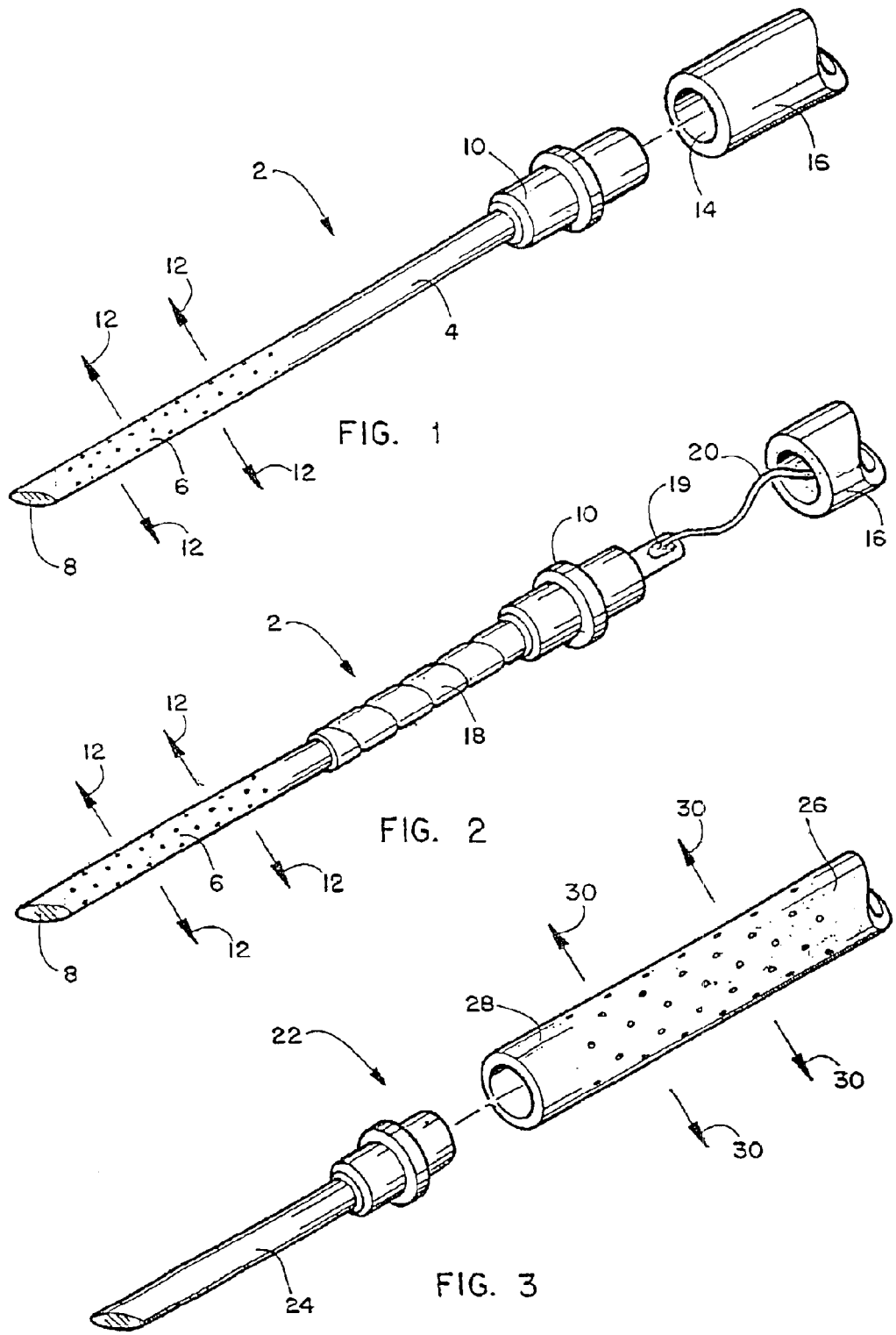

APPARATUS WITH WEEPING TIP AND METHOD OF USE

CROSS REFERENCE TO RELATED APPLICATIONS

The present application is a continuation of U.S. patent application Ser. No. 10/342,023, filed Jan. 14, 2003 now U.S. Pat. No. 6,855,132; which is a continuation of U.S. patent application Ser. No. 09/829,022, filed Apr. 9, 2001, now U.S. Pat. No. 6,547,769; which is a divisional Ser. No. of 09/468,688, filed Dec. 20, 1999, now U.S. Pat. No. 6,241,710.

FIELD OF THE INVENTION

The present invention generally relates to surgical instruments and to instruments used to inject medicaments into a body wall or tissue.

BACKGROUND OF THE INVENTION

The direct introduction of a drug, compound, biologically active peptide or protein into the cells of a patient can have significant therapeutic value. However, this approach also has several drawbacks. Of primary concern is the risk of potential toxicity, particularly at dosages sufficient to produce a biological response to the peptide. From a practical perspective, there is also the problem of the cost associated with isolating and purifying or synthesizing the peptides. Moreover, the clinical impact of the peptides is also limited by their relatively short half-life in vivo, which usually results from their degradation by any proteases present in the target tissue.

For these reasons, introduction of bioactive agents, including proteins, into a patient by delivery of a gene or a cell containing a gene that will express a therapeutic protein in the patient/host is an intriguing alternative to administering the substance. However, to date the principal means for introduction of foreign genetic material into a host has involved the integration of the gene into the host genome by, for example, transforming the host's cells with a viral vector. Direct in vivo gene transfer into postnatal animals has also been reported using DNA encapsulated in liposomes including DNA entrapped in proteoliposomes containing viral envelope receptor proteins.

With respect to delivery systems for genes, means such as viral vectors which introduce the gene into the host's genome can present potential health risks associated with damage to the genetic material in the host cell. Use of cationic liposomes or a biolistic device (i.e., a vaccine "gun" which "shoots" polynucleotides coupled to beads into tissue) to deliver genes in vivo is preparation intensive and, in some cases, requires some experimentation to select proper particle sizes for transmission into target cells. Further, any invasive means of introducing nucleotides (e.g., injection) poses problems of tissue trauma (particularly in long-term therapies) and presents limited access to certain target tissues, such as organs.

Means for non-invasive delivery of pharmaceutical preparations of peptides, such as iontophoresis and other means for transdermal transmission, have the advantage of minimizing tissue trauma However, it is believed that the bioavailability of peptides following transdermal or mucosal transmission is limited by the relatively high concentration of proteases in these tissues.

Injection of "naked DNA" directly into muscle has also been investigated at length. In 1984, work at the NIH was reported which showed that intrahepatic injection of naked, cloned plasmid DNA for squirrel hepatitis into squirrels produced both viral infection and the formation of antiviral antibodies in the squirrels (Seeger, et al, Proc.Nat'l.Acad.Sci USA, 81:5849–5852, 1984). Several years later, Felgner, et al., reported that they obtained expression of protein from "naked" polynucleotides (i.e., DNA or RNA not associated with liposomes or a viral expression vector) injected into skeletal muscle tissue (Felgner, et al., Science, 247:1465, 1990; see also, PCT application WO 90/11092). Felgner, et al. surmised that muscle cells efficiently take up and express polynucleotides because of the unique structure of muscle tissue, which is comprised of multinucleated cells, sarcoplasmic reticulum and a transverse tubular system which extends deep into the muscle cell.

Today, injection of heterologous nucleic acid into cells of striated muscle is generally considered effective to cause expression of DNA or RNA injected into the cells. Gene transfer by injection into subjects of live cells containing nucleic acids that will express therapeutic genes in vivo is also greatly desired, particularly for treatment sites located within a body cavity that can be reached in a relatively non-invasive manner by the use of a catheter. However, gene transfer by injection of nucleic acid or cells containing therapeutic genes is complicated when the injection site is both remote (i.e., located within a body cavity) and in motion. A particularly difficult target for such therapeutic techniques is a beating heart and associated arterial tissue.

Further, even though the amount of the particular isolated therapeutic genes or cells injected into a patient is small, the costs involved in preparation of such therapeutic substances is high. Therefore, any injectate lost during transfer to the patient, for example, by leakage due to too rapid a transfer, represents a considerable monetary loss.

Accordingly, there is still a need in the art for new and better needles and injection systems or surgical assemblages suitable for microinjection of controlled amounts of therapeutic substances without substantial loss of injectate and without substantial damage to tissue, even upon repeat injections. There is a particular need for needles that are adapted for attachment to various types of catheters for such controlled delivery of therapeutic substances at remote locations within the body.

BRIEF DESCRIPTION OF THE INVENTION

The present invention overcomes many of the problems in the art by providing a surgical needle with a weeping tip for microinjection of medicaments into a body surface. The invention surgical needle comprises a nonporous hollow needle shaft having a proximal end adapted to mate with a surgical instrument, a porous distal portion in fluid-tight connection to the needle shaft, and a point that is open, closed or has a solid partial plug. The porous distal portion of the invention needle is adapted to cause a liquid injectate to weep or ooze therefrom multidirectionally under injection pressure while the distal portion and point of the needle are inserted into a body surface. Preferably, the invention needle has features that create a substantially uniform rate of weeping of injectate along the length of the porous distal portion thereof.

The invention surgical needle with weeping tip can be adapted for attachment to such surgical instruments as a syringe, but is preferably adapted for attachment to the distal tip of a catheter In another embodiment according to the present invention, there are provided surgical assemblage(s) useful for injecting a liquid medicament into a remote location in a subject in need thereof. The invention surgical assemblage comprises a needle with a sharp distal point with or without flow-through, and a catheter with a porous distal portion (such as a porous polymer) attached to the distal end of the needle, wherein the porous distal portion of the catheter is adapted to cause a liquid injectate to weep or ooze multi-directionally therefrom into surrounding tissue under injection pressure while inserted into a body surface. The remainder of the catheter is non-porous to assure that the medicament will be delivered only to tissue in contact with the porous portion of the catheter.

The invention surgical needle and/or surgical assemblage is ideally suited for injection into tissue of medicaments containing nucleic acid encoding a therapeutic agent (or cells containing such nucleic acid). For example, the invention needle (when attached to an appropriate catheter) or invention surgical assemblage can be used to inject medicament(s) into the wall of a beating heart or other internal organ, without substantial loss of the medicament at the surface of the body wall and without substantial damage to tissue at the injection site caused by injectate.

Accordingly, in another embodiment according to the present invention, there are provided methods for injecting a medicament into tissue in a subject in need thereof. The invention injection method comprises inserting the distal portion of the invention needle into the tissue of the subject and causing a therapeutic amount of the medicament to ooze multidirectionally from the needle into the tissue without substantial leakage or loss of the medicament at the surface of the tissue. The invention method using the invention needle (or surgical assemblage) with porous distal portion is designed for injection of minute amounts of fluid into tissue or a body wall, hence the use of the term "microinjection" herein.

In another embodiment according to the present invention, there are provided methods for injecting a medicament into a subject in need thereof comprising inserting the distal portion of the invention needle into an interior body wall or tissue of the subject and applying sufficient pressure to a liquid medicament in fluid communication with the distal portion of the needle to expel the medicament such that the medicament weeps multidirectionally from the pores in the distal portion thereof into the interior body wall or tissue without substantial leakage or loss of the medicament at the surface of the body wall. The invention methods are particularly useful for injecting medicament(s) into an interior body wall or tissue that is subject to motion, for example, the wall of a beating heart during electrophysiologic testing, transmyocardial revascularization, and the like.

In yet another embodiment, the present invention provides a method for injecting a medicament into tissue in a subject in need thereof comprising: inserting the distal portion of an invention needle into the tissue of the subject and causing a therapeutic amount of the medicament to ooze multidirectionally from the needle into the tissue without substantial damage to the tissue of the subject caused by injectate.

It is a particular object of the present invention to provide devices and methods useful for simultaneously injecting a medicament from multiple orifices along an injection course, rather than delivering a bolus injection, as is the case with traditional hypodermic needles.

BRIEF DESCRIPTION OF THE FIGURE

FIG. 1 is a schematic drawing showing an exploded view of the invention needle with weeping tip and a catheter to which it attaches.

FIG. 2 is a schematic drawing showing the invention needle with the electrical connector for attachment to an electrocardiogram.

FIG. 3 is a schematic drawing showing the invention surgical assemblage comprising a catheter and a needle, wherein the porous distal portion is located in the flexible catheter.

DETAILED DESCRIPTION OF THE INVENTION

The present invention overcomes many of the problems in the art by providing a surgical needle with a weeping tip for microinjection of medicaments into a body surface. The invention surgical needle comprises a nonporous hollow needle shaft having a proximal end adapted to mate with a surgical instrument, a porous distal portion in fluid-tight connection to the needle shaft, and a point that is open, closed, or has a solid partial plug. The distal portion of the invention needle is adapted to cause a liquid injectate to weep or ooze therefrom multidirectionally under injection pressure while the distal portion and point of the needle are inserted into a body surface. Typically, the length of the porous distal portion of the needle is determined by its intended use (e.g., whether intended for injecting medicament into a blood vessel or into a kidney, and the like). However, the porous distal portion is generally about 1 mm to about 20 mm in length and has pores with an average largest dimension in the range from about 1.0 micron to about 200 microns, for example, in the range from about 3 microns to about 100 microns, or from about 5 microns to about 75 microns.

The invention surgical needle with weeping tip can be adapted for attachment to such surgical instruments as a syringe, but is preferably adapted for attachment to the distal tip of a nonporous catheter. The assemblage of the needle and catheter is preferably steerable. For example, the needle can be attached to the distal tip of a steerable catheter (i.e., comprising a steering mechanism at the handle for controlling deflection of the distal tip section of the catheter shaft), such as is known in the art for injection of medicaments into a remote body cavity or organ wall. Alternatively, the needle can be attached to a catheter with a porous distal portion and then the combination can be introduced into a steerable guidance catheter, such as is used in such surgical techniques as angioplasty, transmyocardial revascularization (TMR), percutaneous transmyocardial revascularization (PTMR), and the like, to direct the needle and catheter to the appropriate site for injection of a medicament. Guidance catheters suitable for use in the invention assemblages and methods are commercially available, for example from such vendors as Eclipse Surgical Technologies (Sunnyvale, Calif.) and CardioGenesis Corp. (Sunnyvale, Calif.).

In one embodiment according to the present invention, the surgical needle is fabricated from a metal commonly used to make surgical needles, such as stainless steel, nitinol, tantalum, elgiloy, and the like, and provided with a distal portion having a multiplicity of pores, while the proximal portion of the needle (i.e., the nonporous hollow needle shaft) is fluid-tight to prevent leakage of fluid therefrom. Consequently, in use it is important to insert the complete porous distal portion of the needle into tissue before and during injection of a medicament.

In another embodiment according to the present invention, the porous distal portion of the surgical needle is adapted to create decreasing hydraulic impedance on injectate moving therethrough towards the point to cause a substantially uniform rate of weeping of injectate from the porous distal portion along the length thereof. The decrease in hydraulic impedance can be of any type, for example, linear, exponential, Gaussian, and the like, and with a gradient in either longitudinal direction.

For example, to create decreasing hydraulic impedance along the length of the porous portion, the size and/or number of the pores in the porous distal portion can increase along its length from the proximal end towards the point. Adjustment of the porosity along the length of the porous distal portion may also be in conjunction with an increasing interior diameter along the length of the porous portion from the proximal end towards the point as needed to offset a falling off of injection pressure on fluid exiting towards the distal end of the device. Alternatively, if a different gradient of injectate is desired, the pore number and/or size can be arranged in any direction suitable to accomplish such a gradient.

The sharp point of the invention needle can be open, closed, or fitted with a solid partial plug to prevent the injectate from exiting as a single jet. If the point of the needle is open, the rate of flow from the open point can also be controlled by adjustment of the hydraulic impedance along the length of the distal portion of the needle to prevent the rate of fluid flow at the tip from substantially exceeding the rate of fluid flow along the porous portion adjacent to the point of the needle.

Alternatively, the point of the needle can be open, but restricted by a solid partial plug so that the distal tip of the needle is designed to operate similarly to the tip of a garden nozzle wherein the solid partial plug cooperates with the open tip to restrict exit of fluid, thereby preventing exit of the fluid as a single jet.

In another embodiment wherein the needle has an open tip, the tip (and a distal portion of the needle shaft) can be loosely covered or loosely sheathed with a porous material, such as the porous sintered metal mesh described above to create the porous distal portion of the needle. In this embodiment, the sheath is attached (e.g., fused or welded) to the needle shaft to create the porous portion from which injectate will weep or ooze (i.e., from the pores in the porous sheath).

The proximal end of the invention needle shaft is provided with a connector, such as a flange, hub, or the like, as is known in the art, for removable attachment of the needle to a surgical instrument, such as a syringe or a catheter. The surgical instrument serves as a reservoir for the fluid medicament. Therefore, the connector is such that there is fluid communication between the needle and the surgical instrument. In use, the invention needle is mounted on the distal tip of the surgical instrument, which is adapted to apply or transmit pressure to the medicament within the nonporous hollow shaft of the needle.

The distal portion of the needle can be fabricated from any of a number of different "open cell" porous materials (i.e., materials in which the pores are interconnecting). For example, the distal portion can be fabricated from a porous sintered metal, such as forms a non-woven matrix of metal fibers selected from such metals as stainless steel, tantalum, elgiloy, nitinol, and the like, and suitable combinations of any two or more thereof. Generally, the metal fibers will have a diameter in the range from about 1.0 micron to about 25 microns. A non-woven matrix of metal fibers having these desired properties that can be used in manufacture of the porous distal portion of the invention needle is available from the Bekaeart Corporation (Marietta, Ga.), and is sold under the trademark, BEKIPOR® filter medium.

The distal porous portion of the needle can also be fabricated from such porous materials as a porous polymer, such as a porous polyimide, polyethylene, polypropylene, polytetrafluroethylene, and the like. Such porous polymers are disclosed, for example, in U.S. Pat. No. 5,913,856, which is incorporated herein by reference in its entirety. Alternatively, a porous ceramic can be used, such as is known in the art for use in ceramic filters and separation membranes, or a porous metal (also known as an expanded metal) or carbon, such as is known in the art for use in filters or bone grafts. For example, Mott Corporation (Farmington, Conn.) manufactures porous metals for use in various types of filters.

If the porous filter medium is flexible, the distal portion of the invention needle can be fabricated by wrapping the filter medium, which is available commercially as a flat sheet, one or more times around an axis while creating a hollow central core. The porous distal portion of the needle can then be fused in fluid-tight fashion (e.g. welded) to a non-porous hollow needle shaft using methods known in the art. To create a porous portion of the needle having decreasing impedance to fluid flow, a porous filter medium or metal mesh having an appropriate porosity gradient can be employed in fabrication of the porous portion.

Alternatively, a porous distal portion for the invention needle can be created from a non-porous material (e.g., a metal) using a cutting laser and techniques known in the art to punch pores into the needle segment (i.e. by a process of laser etching). For example, the nonporous hollow shaft, porous portion, and point of the invention needle can be fabricated of metal in a single piece, for example, from a conventional hypotube. In this scenario, a metal-cutting laser is used to create a segment of the needle that has appropriate porosity, for example, a porosity gradient within a portion of the needle as disclosed herein to equalize fluid impedance along the length of the porous portion of the needle.

In any event, the porosity of the distal portion is generally in the range from about 50% to about 85%, for example, at least about 70%.

Thus, the multidirectional flow of medicament from the needle is controlled by a number of factors, for example, the size, multiplicity and arrangement of the pores in the distal portion, the viscosity of the liquid medicament, the pressure applied to the medicament via the surgical instrument to which it is attached (i.e., the "injection pressure"), and the like. Those of skill in the art will know how to select and combine these factors to assure that the medicament weeps multidirectionally from the pores in the distal portion of the needle into tissue into which it is inserted without substantial surface leakage or tissue damage attributable to the injectate. For example, by balancing these factors, the flow of a liquid medicament from the needle can be adjusted to be at a rate slow enough for the injectate to be absorbed into tissue in the injection site without substantial disruption of cellular and membrane structures as would be caused by bolus or rapid injection, especially from a needle having a single opening. A rate of injection in the range from about 0.1 cc per second to about 2.0 cc per second, for example, from about 0.5 cc per second to about 1.0 cc per second is generally suitable to accomplish these goals.

In the embodiment of the invention illustrated in FIG. 1 herein, needle 2 has a nonporous hollow needle shaft, a porous distal portion 6 having inter-connecting pores and a closed sharp tip 8. Injectate 12 oozes from the pores in the distal portion under injection pressure. The sharp tip 8 of needle 2 is closed so that no injectate flows from the point of the needle. The proximal end of needle 2 is fitted with flange 10 for removable attachment to a catheter. The distal end of catheter 16, which has at least one open lumen 14 for passage of injectate into needle 2 attaches to the proximal end of needle 2. In other embodiments, a hub for mating with a syringe is substituted for the flange at the proximal end of the needle.

In another embodiment according to the present invention, the invention needle further comprises one or more sensor connectors for electrical attachment to an electrocardiogram. The electrocardiogram can be used to determine contact between the needle tip and the tissue, or if multiple electrodes are present, to determine the depth of penetration. In the embodiment shown in FIG. 2, the exterior of the needle shaft (not visible in this Figure) is coated with an insulator 18 and the connector 19 is attached directly to the proximal end (uncoated) of the needle shaft. Electrical lead 20 can be threaded down the lumen of a catheter for attachment to an electrocardiogram. Multiple leads can also be used in order to determine depth of the needle. In this configuration, the electrocardiogram is recorded from all leads. The larger signal is present from those ECG leads that are intramyocardial. Alternatively, the connector can be attached to the interior of the tip of the needle with an insulated connecting wire running down the hollow interior of the needle and catheter for attachment to an electrocardiogram. In this embodiment the needle itself acts as the electrode for the electrocardiogram and can be used for monopolar sensing of electrical currents or impedance within the heart, brain, nerves, proximal arteries, and the like.

For bipolar sensing a return electrode can be provided by placing an ECG pad in electrical connection with the electrocardiogram on the exterior of the patient, for example on the exterior of the chest wall. It is also contemplated within the scope of the invention that a second electrode or sensor connector can be attached to the needle, for example to the exterior of the needle, spaced apart from the first electrode by at least about 0.5 mm, so as to provide two electrodes for sensing electrical currents within a subject's bodily organs. It is also possible that an electrode permanently implanted in a subject, such as belongs to a pacemaker, can be used as the return lead for remote bipolar sensing.

The advantages of using the invention needles to perform sensing are several. For example, for injection into a muscle or other organ that has electrical impulses running through it, an electrocardiogram sensor attached to the invention needle can be used to confirm contact of the needle tip or proper insertion of the needle into the body wall of interest (e.g., the wall of a beating heart) before injection of the medicament into a treatment site. The depth of needle insertion into the tissue is determined by an array of electrodes. Those of skill in the art will realize that the invention needle having attached electrocardiogram sensor can also be used to judge whether such a prospective injection site is electrically active or not (i.e., whether the tissue is dead, hibernating due to lack of oxygen, or alive), and the like.

In another embodiment according to the present invention, there are provided surgical assemblages useful for microinjection of a liquid medicament into a remote location in a subject in need thereof. The invention surgical assemblage comprises a needle with a sharp distal point, and a catheter with a porous distal portion attached to the distal end of the needle, wherein the porous distal portion is adapted to cause a liquid injectate to weep or ooze multidirectionally therefrom into surrounding tissue under injection pressure while the porous distal portion of the catheter is inserted into a body surface. The catheter in the invention surgical assemblage can be a steerable catheter having a steering mechanism at the handle for controlling deflection of the distal tip section of the catheter shaft, thereby, in effect, creating a "steerable needle."

Alternatively, the invention surgical assemblage can further comprise a guidance catheter of the type known in the art for guiding instruments used in angioplasty, as is described more fully hereinabove. In this embodiment, the needle and catheter with porous distal portion is introduced into (i.e., threaded through) the guidance catheter so that the needle and catheter with porous distal portion can be directed to the site of injection (e.g., threaded through a desired section of tissue) using the steerable guidance catheter.

Preferably, the porous distal portion of the catheter is made of a flexible porous polymer, such as a porous polyimide, polyethylene, polytetrafluoroethylene, or polypropylene, and the like. The porous distal portion may further have features that create increasing hydraulic impedance on injectate moving therethrough towards the needle, thereby causing uniform flow of the injectate therefrom along the length of the porous distal portion as the injectate moves therethrough towards the needle to offset the falling off of injection pressure on fluid as it moves towards the point of the device. The flexibility of the porous segment in the assemblage facilitates injection of medicaments along a non-linear path.

As with the porous portion of the invention surgical needle described above, the size, and/or number of pores in the porous portion of the catheter in the invention surgical assemblage can be selected to create any desired gradient of injectate along the course of the injection path. For example, the size, and/or number of pores can decrease along the length of the porous portion moving towards the connection with the needle to allow for a substantially uniform rate of injectate weepage along the length of the porous portion. In this configuration, therefore, once the needle is used to thread the porous portion of the catheter through the tissue to be treated, a substantially uniform rate of fluid weepage into surrounding tissues can be obtained along the injection course. Alternatively, or in conjunction with such a porosity gradient, the porous distal portion can also have a decreasing interior diameter along its length moving from the proximal end towards the connection with the needle to accomplish the same goal.

FIG. 3 herein illustrates the invention surgical assemblage 22. Non-porous needle 24 with a closed tip is attached to the distal end of flexible catheter 26, which has a porous distal portion 28. Injectate 30 weeps from the pores in the flexible distal portion 28 of catheter 26.

In another embodiment according to the present invention, there are provided methods for injecting a medicament into an body wall in a subject in need thereof. The invention method comprises inserting the porous distal portion of the invention needle into the tissue of the subject and applying sufficient injection pressure to a liquid medicament in fluid communication with the porous distal portion of the needle to cause the medicament to ooze multidirectionally from the pores in the needle into the tissue. Alternatively, the invention surgical assembly, wherein the porous portion is not contained in the needle, but is a porous distal portion of an otherwise nonporous catheter, can be used in the invention injection methods to similar effect. If the point and porous portion of the needle or surgical assembly are inserted into the tissue before the medicament is injected, the injection of medicament is performed without substantial leakage or loss of medicament at the surface of the tissue or interior body wall.

As used herein, the term "medicament(s)" includes all types of liquid substances (e.g., including solutions and suspensions) that have a beneficial or therapeutic effect. Non-limiting examples of medicaments suitable for use in the invention methods include biologically active agents, such as small molecule drugs, proteinaceous substances, polynucleotides or nucleic acids (e.g. heterologous DNA, or RNA) and vectors, liposomes, and the like, containing such nucleic acids or polynucleotides, as well as liquid preparations or formulations thereof.

The invention methods and devices are designed for injection of minute amounts of fluid medicaments into tissue or a body wall, for example, an interior body wall. Hence the use of the term "microinjection" herein. For example, the therapeutic amount of the medicament to be administered according to the invention method will vary depending upon the therapeutic goal to be accomplished, the size and age of the subject, the pharmacokinetics of the injectate, and the like. However, a therapeutic amount according to the present invention is typically in the range from about 0.5 cc to about 2.0 cc.

Under injection pressure exerted upon a fluid medicament within the invention needle or surgical assemblage, the injectate will weep or ooze multidirectionally from the porous distal portion into surrounding tissue into which it is inserted, but should be prevented from exiting from the proximal portions of the invention devices. Flow of the injectate into the surrounding tissue is contemplated to be at a slow rate, for example, in the range from about 0.1 cc per second to about 2.0 cc per second to allow absorption of and dissipation the medicament into the tissue without substantial tissue damage caused by the injectate, (e.g., pooling of the medicament is thereby avoided). So long as the injectate contains no particles (e.g. cells) larger than the pores in the distal portion of the needle, overall flow of the medicament into tissue will be proportional to the amount of pressure applied on the injectate.

However, unless the porous portion of the invention device is adapted to cause a increasing gradient of impedance to fluid flow as the fluid moves distally through the porous portion (i.e., towards the point of the needle), the medicament will not weep at a uniform flow rate along the length of the porous portion.

In practice of the invention methods, it is presently preferred that the combination of the needle and the surgical instrument to which it is attached be selected so that the amount of the medicament that oozes from the pores of the needle can be controlled by the operator. For example, if a measured amount of the medicament is placed for delivery into a calibrated chamber of the surgical instrument and/or hollow of the needle, pressure on the medicament in the chamber sufficient to deliver 2 cc of the medicament from the pores of the distal portion of the needle while the distal portion is inserted into tissue of the subject will substantially assure that the subject receives 2 cc of the medicament. This feature of the invention devices and methods is particularly advantageous when it is important to closely monitor the amount of the medicament delivered to the subject, for example, to avoid waste of the medicament, to accurately judge the efficacy of the treatment, and the like.

The invention methods can be used to deliver to a subject in need of gene therapy an therapeutic amount of a medicament containing an isolated therapeutic nucleic acid sequence, or a vector, liposome, or cell, and the like, containing such a nucleic acid sequence operatively associated with regulatory nucleic acid for expression of the encoded therapeutic protein. The invention devices and methods can be used to promote gene therapy by injection of such medicaments even when the injection site is located internally and/or is in constant motion. Therefore, in another embodiment according to the present invention, there are provided methods for injecting a therapeutic amount of a medicament into an interior body wall or tissue of a subject in need thereof. In this embodiment, the invention method comprises inserting the distal portion of the invention needle into an interior body wall or tissue of the subject and applying sufficient pressure to a liquid medicament in fluid communication with the distal portion of the needle to expel a therapeutic amount of the medicament such that the medicament weeps multidirectionally from the pores in the distal portion thereof into the interior body wall or tissue without substantial leakage or loss of the medicament at the surface of the body wall. The body wall can be located within a natural body cavity or a surgically created opening.

The invention method utilizing the needle with weeping tip is particularly useful for injection of medicaments into the wall of an interior organ that is subject to motion during the injection procedure, for example, the wall of a beating heart or adjacent arterial walls during electrophysiologic testing, transmyocardial revascularization, and the like. Additional internal organs subject to movement into which injections can be made using the invention methods include the stomach, esophagus, gallbladder, liver, bowel, kidney, lung, and the like.

By "isolated polynucleotide" or "isolated nucleic acid" or isolated nucleic acid sequence" is meant a polynucleotide that is not immediately contiguous with both of the coding sequences with which it is immediately contiguous (one on the 5' end and one on the 3' end) in the naturally occurring genome of the organism from which it is derived. The term therefore includes, for example, a recombinant DNA which is incorporated into a vector; into an autonomously replicating plasmid or virus; or into the genomic DNA of a prokaryote or eukaryote; or which exists as a separate molecule (e.g. a cDNA) independent of other sequences. Therapeutic nucleic acids contemplated for use in the practice of the present invention are intended to include those which encode products which are toxic to the cells in which they are expressed; those that encode products which impart a beneficial property to a subject; and those that transcribe nucleic acids which modulate transcription and/or translation of endogenous genes.

Preferred examples of suitable therapeutic nucleic acids for administration into cardiac tissues using the invention devices and methods include those encoding growth factors that enhance apoptosis and cell growth, such as bFGF (basic fibroblast growth factor, also known as FGF-2), aFGF (also known as FGF-1), EGF (epithelial growth factor), VEGF (vascular epithelial growth factor), angiostatin, ecchystatin, IGFs (insulin-like growth factors), and the like. These agents can be used to enhance or prevent the development of new blood vessels, prevent inflammation (as results from direct injection into the wall of an artery), prevent neointimal hyperplasia, or enhance or prevent the growth of new myocardial cells.

Additional therapeutic nucleic acids useful in the practice of the present invention include genes that encode biologically active proteins of interest, such as, e.g., secretory proteins that can be released from said cell; enzymes that can metabolize a toxic substance to produce a non-toxic substance, or that metabolize an inactive substance to produce a useful substance; regulatory proteins; cell surface receptors; and the like. Useful genes include genes that encode blood clotting factors, such as human factors VIII and IX; genes that encode hormones, such as insulin, parathyroid hormone, luteinizing hormone releasing factor (LHRH), alpha and beta seminal inhibins, and human growth hormone; genes that encode proteins, such as enzymes, the absence of which leads to the occurrence of an abnormal state; genes encoding cytokines or lymphokines such as interferons, granulocytic macrophage colony stimulating factor (GM-CSF), colony stimulating factor-1 (CSF-1), tumor necrosis factor (TNF), and erythropoietin (EPO); genes encoding inhibitor substances such as $alpha_1$-antitrypsin; genes encoding substances that function as drugs, e.g., genes encoding the diphtheria and cholera toxins; and the like.

Typically, nucleic acid sequence information for proteins encoded by therapeutic nucleic acid(s) contemplated for use employed herein can be located in one of many public access databases, e.g., GENBANK, EMBL, Swiss-Prot, and PIR, or in related journal publications. Thus, those of skill in the art have access to sequence information for virtually all known genes. Those of skill in the art can obtain the corresponding nucleic acid molecule directly from a public depository or from the institution that published the sequence. Optionally, once the nucleic acid sequence encoding a desired protein has been ascertained, the skilled artisan can employ routine methods, e.g., polymerase chain reaction (PCR) amplification, to isolate the desired nucleic acid molecule from the appropriate nucleic acid library. Thus, all known nucleic acids encoding proteins of interest are available for use in the methods and products described herein.

Additional components that can optionally be incorporated into the invention constructs include selectable markers and genes encoding proteins required for retroviral packaging, e.g., the pol gene, the gag gene, the env gene, and the like.

Selectable markers contemplated for use in the practice of the present invention include antibiotic resistance genes, genes that enable cells to process metabolic intermediaries, and the like. Exemplary antibiotic resistance genes include genes which impart tetracycline resistance, genes that impart ampicillin resistance, neomycin resistance, hygromycin resistance, puromycin resistance, and the like.

Optionally, the cells can be obtained from the subject or host (i.e., rather than a donor), modified as above, and then reintroduced into the subject using the invention devices and methods. For example, therapeutic nucleic acid can be introduced directly into cells obtained from a subject and the modified cells can be then injected into the subject. The therapeutic nucleic acid may be stably incorporated into cells or may be transiently expressed using methods known in the art.

Modified cells are cultivated under growth conditions (as opposed to protein expression conditions) until a desired density is achieved. Stably transfected mammalian cells may be prepared by transfecting cells with an expression vector having a selectable marker gene (such as, for example, the gene for thymidine kinase, dihydrofolate reductase, neomycin resistance, and the like), and growing the transfected cells under conditions selective for cells expressing the marker gene. To prepare transient transfectants, mammalian cells are transfected with a reporter gene (such as the E. coli β-galactosidase gene) to monitor transfection efficiency. Selectable marker genes are typically not included in the transient transfections because the transfectants are typically not grown under selective conditions, and are usually analyzed within a few days after transfection.

The concept of gene replacement therapy for humans involves the introduction of functionally active nucleic acids into the somatic cells of an affected subject to correct a gene defect or deficiency. Genes that encode useful "gene therapy" proteins that are not normally transported outside the cell can be used in the invention if such genes are "functionally appended" to, or operatively associated with, a signal sequence that can "transport" the encoded product across the cell membrane. A variety of such signal sequences are known and can be used by those skilled in the art without undue experimentation.

Regulatory elements employed in the practice of the present invention are operably linked to a suitable promoter for transcription of therapeutic nucleic acid product(s). As used herein, the term "promoter" refers to a specific nucleic acid sequence recognized by RNA polymerase, the enzyme that initiates RNA synthesis. The promoter sequence is the site at which transcription can be specifically initiated under proper conditions. When exogenous nucleic acid(s), operatively linked to a suitable promoter, are introduced into the cells of a suitable host, expression of the exogenous nucleic acid(s) can be controlled in many, but not all cases, by the presence of ligands, which are not normally present in the host cells.

Promoters contemplated for control of expression of exogenous nucleic acids employed in the practice of the present invention include inducible (e.g., minimal CMV promoter, minimal TK promoter, modified MMLV LTR), constitutive (e.g., chicken β-actin promoter, MMLV LTR (non-modified), DHFR), and/or tissue specific promoters.

Inducible promoters contemplated for use in the practice of the present invention comprise transcription regulatory regions that function maximally to promote transcription of mRNA under inducing conditions. Examples of suitable inducible promoters include DNA sequences corresponding to: the E. coli lac operator responsive to IPTG (see Nakamura et al., Cell, 18:1109–1117, 1979); the metallothionein promoter metal-regulatory-elements responsive to heavy-metal (e.g., zinc) induction (see Evans et al., U.S. Pat. No. 4,870,009), the phage T7lac promoter responsive to IPTG (see Studier et al., Meth. Enzymol, 185: 60–89, 1990; and U.S. Pat. No. 4,952,496), the heat-shock promoter; the TK minimal promoter; the CMV minimal promoter; a synthetic promoter; and the like.

Exemplary constitutive promoters contemplated for use in the practice of the present invention include the CMV promoter, the SV40 promoter, the DHFR promoter, the mouse mammary tumor virus (MMTV) steroid-inducible promoter, Moloney murine leukemia virus (MMLV) promoter, elongation factor 1a (EF 1a) promoter, albumin promoter, APO A1 promoter, cyclic AMP dependent kinase II (CaMKII) promoter, keratin promoter, CD3 promoter, immunoglobulin light or heavy chain promoters, neurofiliment promoter, neuron specific enolase promoter, L7 promoter, CD2 promoter, myosin light chain kinase promoter, HOX gene promoter, thymidine kinase (TK) promoter, RNA Pol II promoter, MYOD promoter, MYF5 promoter, phosphoglycerokinase (PGK) promoter, Stf1 promoter, Low Density Lipoprotein (LDL) promoter, chicken β-actin promoter (e.g., used in conjunction with an ecdysone response element), and the like.

As readily understood by those of skill in the art, the term "tissue specific" refers to the substantially exclusive initiation of transcription in the tissue from which a particular promoter that drives expression of a given gene is derived (e.g., expressed only in T-cells, endothelial cells, smooth muscle cells, and the like). Exemplary tissue specific promoters contemplated for use in the practice of the present invention include the GH promoter, the NSE promoter, the GFAP promoter, neurotransmitter promoters (e.g., tyrosine hydroxylase, TH, choline acetyltransferase, ChAT, and the like), promoters for neurotropic factors (e.g., a nerve growth factor promoter, NT-3, BDNF promoters, and the like), and so on.

As used herein, the phrase "operatively associated with" refers to the functional relationship of DNA with regulatory and effector sequences of nucleic acids, such as promoters, enhancers, transcriptional and translational stop sites, and other signal sequences. For example, operative linkage of DNA to a promoter refers to the physical and functional relationship between the DNA and promoter such that the transcription of such DNA is initiated from the promoter by an RNA polymerase that specifically recognizes, binds to and transcribes the DNA.

Gene transfer vectors (also referred to as "expression vectors") contemplated for use herein are recombinant nucleic acid molecules that are used to transport nucleic acid into host cells for expression and/or replication thereof. Expression vectors may be either circular or linear, and are capable of incorporating a variety of nucleic acid constructs therein. Expression vectors typically come in the form of a plasmid that, upon introduction into an appropriate host cell, results in expression of the inserted nucleic acid.

Suitable expression vectors for use herein are well known to those of skill in the art and include recombinant DNA or RNA construct(s), such as plasmids, phage, recombinant virus or other vectors that, upon introduction into an appropriate host cell, result(s) in expression of the inserted DNA. Appropriate expression vectors are well known to those of skill in the art and include those that are replicable in eukaryotic cells and/or prokaryotic cells and those that remain episomal or those which integrate into the host cell genome. Expression vectors typically further contain other functionally important nucleic acid sequences encoding antibiotic resistance proteins, and the like.

The amount of therapeutic nucleic acid introduced into a subject can be varied by those of skill in the art. For example, when a viral vector is employed to achieve gene transfer, the amount of nucleic acid introduced can be varied by varying the amount of plaque forming units (FU) of the viral vector.

Exemplary eukaryotic expression vectors include eukaryotic constructs, such as the pSV-2 gpt system (Mulligan et al., *Nature* 277:108–114, 1979); pBlueSkript (Stratagene, La Jolla, Calif.), the expression cloning vector described by Genetics Institute (*Science* 228:810–815, 1985), and the like. Each of these plasmid vectors is capable of promoting expression of the protein product of the nucleic acid of interest.

Suitable means for introducing (transducing) expression vectors containing therapeutic nucleic acid constructs into cells of a subject treated according to the invention methods include infection employing viral vectors (see, e.g., U.S. Pat. Nos. 4,405,712 and 4,650,764). The transduced nucleic acid can optionally include sequences which allow for its extrachromosomal (i.e., episomal) maintenance, or the transduced nucleic acid can be donor nucleic acid that integrates into the genome of the host.

In a specific embodiment, a gene transfer vector contemplated for use herein is a viral vector, such as Adenovirus, adeno-associated virus, a herpes-simplex virus based vector, a synthetic vector for gene therapy, and the like (see, e.g., Suhr et al., *Arch. of Neurol.* 50:1252–1268, 1993). Preferably, a gene transfer vector employed herein is a retroviral vector. Retroviral vectors contemplated for use herein are gene transfer plasmids that have an expression construct containing an exogenous nucleic acid residing between two retroviral LTRs. Retroviral vectors typically contain appropriate packaging signals that enable the retroviral vector, or RNA transcribed using the retroviral vector as a template, to be packaged into a viral virion in an appropriate packaging cell line (see, e.g., U.S. Pat. No. 4,650,764).

Suitable retroviral vectors for use herein are described, for example, in U.S. Pat. Nos. 5,399,346 and 5,252,479; and in WIPO publications WO 92/07573, WO 90/06997, WO 89/05345, WO 92/05266 and WO 92/14829, each of which is hereby incorporated herein by reference, in its entirety. These documents provide a description of methods for efficiently introducing nucleic acids into human cells using such retroviral vectors. Other retroviral vectors include, for example, mouse mammary tumor virus vectors (e.g., Shackleford et al *PNAS, USA,* 85:9655–9659, 1988), human immunodeficiency virus (e.g., Naldini et al *Science* 272:165–320, 1996), and the like.

Various procedures are also well-known in the art for providing helper cells which produce retroviral vector particles that are essentially free of replicating virus. See, for example, U.S. Pat. No. 4,650,764; Miller, *Human Gene Therapy,* 1:5–14, 1990; Markowitz, et al., *Journal of Virology,* 61(4):1120–1124, 1988; Watanabe, et al., *Molecular and Cellular Biology,* 3(12):2241–2249, 1983; Danos, et al., *PNAS,* 85:6460–6464, 1988; and Bosselman, et al., *Molecular and Cellular Biology,* 7(5):1797–1806, 1987, which disclose procedures for producing viral vectors and helper cells that minimize the chances for producing a viral vector that includes a replicating virus.

Recombinant retroviruses suitable for carrying out the invention methods are produced employing well-known methods for producing retroviral virions. See, for example, U.S. Pat. No. 4,650,764; Miller, supra 1990; Markowitz, et al., supra 1988; Watanabe, et al., supra 1983; Danos, et al., *PNAS,* 85:6460–6464, 1988; and Bosselman, et al., *Molecular and Cellular Biology,* 7(5): 1797–1806, 1987.

By introducing all of the necessary regulatory machinery, plus exogenous nucleic acid, selectable markers, and nucleic acid encoding invention chimeric protein, e.g., into a MARV retrovirus, highly efficient insertion of exogenous nucleic acids into targeted cells can be achieved.

Thus, the above-described viral constructs address several important problems confronted in the use of retroviruses in application of therapeutic gene transfer strategies to a variety of human diseases. For example, the retroviral vectors of the invention are capable of prolonged gene expression under conditions where conventionally integrated retroviruses are no longer transcriptionally active.

As used herein, when referring to nucleic acids, the phrase "exogenous to said mammalian host" or simply "exogenous" refers to nucleic acids not naturally found at levels sufficient to provide a function in the particular cell where transcription is desired. For example, exogenous nucleic acids can be either natural or synthetic nucleic acids, which are introduced into the subject in the form of DNA or RNA. The nucleic acids of interest can be introduced directly or indirectly into a subject, for example, by the transfer of transformed cells into a subject using invention methods.

As employed herein, the terms "subject" and "host" refer to a mammalian patient in need of administration of a medicament. The subject mammals include: humans; domesticated animals, e.g., rat, mouse, rabbit, canine, feline, and the like; farm animals, e.g., chicken, bovine, ovine, porcine, and the like; animals of zoological interest, e.g., monkey, baboon, and the like While the invention has been described in detail with reference to certain preferred embodiments thereof, it will be understood that modifications and variations are within the spirit and scope of that which is described and claimed.

What is claimed is:

1. A method of delivering a medical substance to a patient comprising:

providing a delivery device having a proximal end and a porous distal tip and a single lumen extending therebetween, wherein said porous distal tip comprises a plurality of microholes distributed substantially uniformly along said porous distal tip;

introducing said delivery device into said patient and guiding said distal tip to an injection site in said patient;

initiating an injection of medical substance through said single lumen of said delivery device, said single lumen having a substantially constant diameter along an entire length of said porous distal tip; and, at least partially closing an end region of said distal tip so as to cause said medical substance to weep and ooze from said plurality of microholes of said distal tip to said injection site in said patient.

2. A method according to claim 1, wherein causing said medical substance to weep includes causing said medical substance to exit microholes having a diameter within the range of about 1.0 micron to about 200 microns.

3. A method according to claim 1, wherein the introducing of said delivery device into said patient includes introducing said delivery device into a body lumen of a patient.

4. A method according to claim 1, wherein at least partially closing an end region of said distal tip includes providing a restrictive tip on said delivery device.

5. A method according to claim 4, wherein providing a restrictive tip on said delivery device includes providing a partially solid plug mechanism at said porous distal tip.

6. A method according to claim 3, wherein the introducing of said delivery device into a body lumen includes introducing a catheter into said body lumen.

7. A method according to claim 2, wherein said microholes have an average diameter of approximately 50 microns.

8. A method according to claim 1, wherein the providing of a delivery device includes providing a delivery device wherein said distal tip has a length in a range of approximately 1 mm to about 20 mm.

9. A method according to claim 1, further comprising maintaining pressure in said delivery device at a state so as to continue to cause said medical substance to weep and ooze from said plurality of microholes of said distal tip throughout substantially an entire injection procedure.

10. A method according to claim 1, further comprising sensing electrical activity of a patient's heart during the initiating of an injection.

11. A method according to claim 1, wherein the initiating of an injection includes initiating an Injection through said delivery device to a patient's heart.

12. A device according to claim 11, wherein the initiating of an injection includes initiating an injection through said delivery device to a patient's beating heart.

13. A method according to claim 1, wherein the initiating of an injection includes delivering said medical substance to an interior organ of said patient.

14. A method according to claim 1, wherein the initiating of an injection includes initiating an injection of an isolated therapeutic nucleic acid sequence.

15. A method according to claim 1, further comprising monitoring the amount of medical substance being injected out of said delivery device.

16. A method according to claim 1, further comprising monitoring the injection pressure during said injection.

17. A device for delivering a medical substance to a patient comprising:

a conduit having a proximal end, a distal end and a single internal lumen disposed therebetween;

said distal end having a porous region disposed thereon; said porous region including a plurality of pores sized and distributed along said porous region; and, said distal end being at least partially closed such that said medical substance is caused to weep and ooze from said distal end of said conduit when pressure is introduced into said device;

a partial plug permanently disposed at a hole at an end of said distal portion so as to prevent flow out of said hole from substantially exceeding a flow through said plurality of pores; and, said distal portion having a substantially constant diameter along its length.

18. A device according to claim 17, wherein said plurality of pores have an average diameter within the range of about 1 micron to about 200 microns.

19. A device according to claim 17, wherein said porous region has a length within a range of about 1 mm to about 20 mm.

20. A device according to claim 17, wherein said conduit is a catheter.

21. A device according to claim 17, wherein said conduit is a needle.

22. A device according to claim 17, wherein said partial plug is configured to cooperate with said hole to restrict exit of said medical substance.

23. A device according to claim 17, wherein said porous region has a porosity in the range of about 50% to about 85%.

24. A device according to claim 17, wherein the porous region is fabricated from a polymer substance.

25. A device according to claim 17, wherein said conduit has a length sufficient for injection of said medical substance at a remote injection site in said patient.

26. A device according to claim 17, wherein said conduit is steerable.

27. A device according to claim 17, further comprising a sensor connected to said conduit.

28. A device according to claim 27, wherein said sensor is a pressure sensor.

29. A method of delivering a medical substance to a patient comprising:

providing a delivery device having a proximal end and a porous distal end and a single lumen extending therebetween, wherein said porous distal end comprises a plurality of microholes distributed substantially uniformly along said porous distal end;

introducing said delivery device into said patient and guiding said distal end to an injection site in said patient;

initiating a flow of an injection of medical substance through said single lumen of said delivery device, said single lumen having a substantially constant diameter along an entire length of said porous distal end; and, restricting said flow at an end region of said distal end so as to cause said medical substance to weep and ooze from said plurality of microholes of said distal end to said injection site in said patient.

30. A method according to claim 29, wherein the restricting of said flow includes partially restricting said flow.

31. A method according to claim 29, wherein the restricting of said flow includes completely restricting said flow.

32. A method according to claim 29, wherein the providing of a delivery device includes providing a catheter.

33. A method according to claim 29, wherein the introducing of said delivery device includes introducing said delivery device into a body lumen of said patient.

34. A method according to claim 33, wherein the introducing of said delivery device into a body lumen includes introducing said delivery device into a blood vessel of said patient.

35. A method according to claim 29, further comprising sensing electrical activity of a patient's heart during the initiating of an injection.

36. A method according to claim 29, wherein the initiating of an injection includes initiating an injection through said delivery device to a patient's heart.

37. A device according to claim 36, wherein the initiating of an injection includes initiating an injection through said delivery device to a patient's beating heart.

38. A method according to claim 29, wherein the initiating of an injection includes delivering said medical substance to an interior organ of said patient.

39. A method according to claim 29, wherein the initiating of an injection includes initiating an injection of an isolated therapeutic nucleic acid sequence.

40. A method according to claim 29, further comprising monitoring the amount of medical substance being in injected out of said delivery device.

41. A method according to claim 29, further comprising monitoring the injection pressure during said injection.

* * * * *